(12) United States Patent
Nichol

(10) Patent No.: US 9,465,365 B2
(45) Date of Patent: Oct. 11, 2016

(54) ELECTRONIC DEVICE CAPABLE OF BEING COUPLED TO A WRISTWATCH

(71) Applicant: Mark Nichol, San Francisco, CA (US)

(72) Inventor: Mark Nichol, San Francisco, CA (US)

( * ) Notice: Subject to any disclaimer, the term of this patent is extended or adjusted under 35 U.S.C. 154(b) by 168 days.

(21) Appl. No.: 14/524,828

(22) Filed: Oct. 27, 2014

(65) Prior Publication Data

US 2015/0117161 A1    Apr. 30, 2015

Related U.S. Application Data

(60) Provisional application No. 61/895,946, filed on Oct. 25, 2013.

(51) Int. Cl.
| | |
|---|---|
| *G04B 47/06* | (2006.01) |
| *G04G 21/04* | (2013.01) |
| *G04G 21/02* | (2010.01) |

(52) U.S. Cl.
CPC ........... *G04B 47/063* (2013.01); *G04G 21/025* (2013.01); *G04G 21/04* (2013.01)

(58) Field of Classification Search
CPC .... G04B 47/00; G04B 47/063; G04G 21/02; G04G 21/025; G04G 21/04
USPC ...................................... 368/10, 11
See application file for complete search history.

(56) References Cited

U.S. PATENT DOCUMENTS

| | | | | |
|---|---|---|---|---|
| 5,481,506 A * | 1/1996 | Kita | ...................... | G04G 21/025 368/10 |
| 5,781,511 A * | 7/1998 | Yasukawa | .......... | A61B 5/02438 368/10 |
| 6,269,053 B1 * | 7/2001 | Kawata | ................. | G04G 17/02 368/10 |
| 6,605,045 B2 * | 8/2003 | Ohsaki | .................. | A61B 5/681 600/503 |
| 7,454,002 B1 | 11/2008 | Gardner et al. | | |
| 8,725,842 B1 | 5/2014 | Al-Nasser | | |
| 2002/0151775 A1 * | 10/2002 | Kondo | ............... | A61B 5/02438 600/344 |
| 2005/0010119 A1 * | 1/2005 | Palti | ................... | A61B 5/02233 600/499 |
| 2005/0162984 A1 | 7/2005 | Wilson | | |
| 2006/0122521 A1 * | 6/2006 | Chen | .................. | A61B 5/02438 600/503 |
| 2006/0133213 A1 * | 6/2006 | Robert | .................... | G04G 21/02 368/11 |
| 2007/0015980 A1 * | 1/2007 | Numada | ................ | A61B 5/489 600/322 |
| 2007/0191718 A1 * | 8/2007 | Nakamura | ........... | A61B 5/0002 600/503 |
| 2011/0003665 A1 * | 1/2011 | Burton | .................... | G04F 10/00 482/9 |
| 2013/0072765 A1 * | 3/2013 | Kahn | ....................... | A61B 5/01 600/301 |
| 2013/0211204 A1 * | 8/2013 | Caduff | ...................... | A45F 3/14 600/300 |

* cited by examiner

*Primary Examiner* — Vit W Miska
(74) *Attorney, Agent, or Firm* — Leydig, Voit & Mayer

(57) ABSTRACT

An electronic device that includes: a housing; an attachment portion capable of coupling the housing to a bottom of a wristwatch to be worn by a wearer; one or more physiological sensors included in the housing that measure one or more physical phenomena corresponding to the wearer of the wristwatch and electronic device coupled to the wristwatch; a memory configured to store data corresponding to the one or more physical phenomena; and a wireless communication device included in the housing for communicating the data to a computing device in wireless communication with the electronic device.

21 Claims, 10 Drawing Sheets

US 9,465,365 B2

ELECTRONIC DEVICE CAPABLE OF BEING COUPLED TO A WRISTWATCH

CROSS-REFERENCE TO RELATED PATENT APPLICATIONS

This patent application claims the benefit of U.S. provisional application No. 61/895,946, filed on Oct. 25, 2013, which is hereby incorporated by reference in its entirety.

BACKGROUND

Today's wrist watches are as much about style and design as they are about time-telling functionality. Watches are made from various precious metals, including steel, gold, and platinum, and have prices that can reach as high as tens of thousands of dollars. Watches come in a myriad of different shapes and forms and represent one's personal style and taste.

Wearable technology, in the form of wearable health and wellness devices, is gaining popularity as people want to track their activity and body metrics. Currently, the leading design in wearable technology is a bracelet that houses various sensors and electronics. The bracelet is worn around a user's wrist. The bracelet can provide useful data and metrics to a user, however, there is only so much real estate on one's wrist and these wearable technology devices compete directly with watches for this space on the body. Lots of wristwatch wearers want to have access to this valuable physiological information, but do not want to take off their expensive, stylish, and/or sentimental wristwatch and replace it with a wearable technology band. Another drawback to conventional approaches is that when a wearable health band's battery dies, the wearable health band loses all functionality because it has no power.

SUMMARY

One embodiment of the disclosures includes an electronic device, comprising: a housing; an attachment portion capable of coupling the housing to a bottom of a wristwatch to be worn by a wearer; one or more physiological sensors included in the housing that measure one or more physical phenomena corresponding to the wearer of the wristwatch and electronic device coupled to the wristwatch; a memory configured to store data corresponding to the one or more physical phenomena; and a wireless communication device included in the housing for communicating the data to a computing device in wireless communication with the electronic device.

Another embodiment of the disclosure includes a method and computer-readable medium for operating an electronic device. The method includes: detecting that the electronic device is being worn a wearer, wherein the electronic device is coupled to a bottom of a wristwatch worn by the wearer; measuring, using one or more physiological sensors included in the electronic device, one or more physical phenomena; storing data corresponding to the one or more physical phenomena in a memory included in the electronic device; and, transmitting the data corresponding to the one or more physical phenomena to a computing device in wireless communication with the electronic device.

DETAILED DESCRIPTION

Embodiments of the disclosure solve the problems of conventional approaches by providing a sensor-filled device that can be attached directly to the bottom of one's wristwatch. In some embodiments, the device is a small, discrete disc-shaped device that attaches to the back of one's wristwatch and houses a collection of sensors that enables wristwatch wearers to continue to wear their wristwatch, while also having access to the physiological data that modern sensors can provide. In some embodiments, the device can be used with virtually any wristwatch, regardless of the wristwatch's shape and how the wristwatch strap connects to the wristwatch case.

Also, as described above, in conventional approaches, when a wearable health band's battery dies, the wearable health band loses all functionality because it has no power. Embodiments of the discover overcome this drawback because, in some embodiments, if the disclosed device does run out of power, the user still has his or her wristwatch on and does not lose the wristwatch's functionality—an important benefit.

Figure 1:
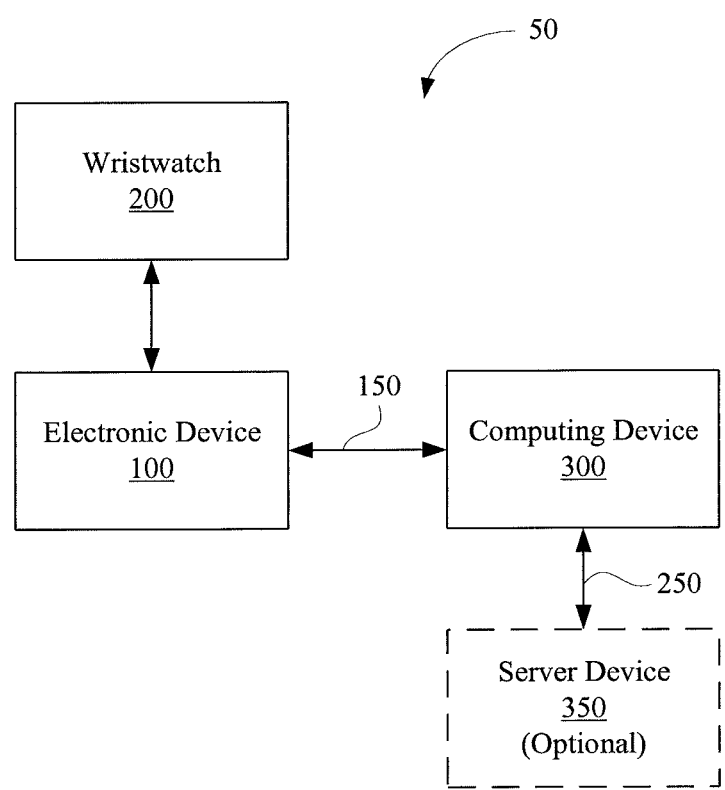
FIG. 1 is a block diagram of a system including an electronic device capable of being coupled to a wristwatch, according to one embodiment of the disclosure.

FIG. 1 is a block diagram of a system 50 including an electronic device 100 capable of being coupled to a wristwatch 200, according to one embodiment of the disclosure. The system also includes a computing device 300 in communication with the electronic device 100 and, optionally, a server device 350 in communication with the computing device 300.

The wristwatch 200 is a standard time-keeping wristwatch. The wristwatch 200 can be made of metal, plastic, or a combination of metal and plastic, or other materials. In some embodiments, the wristwatch 200 does not have embedded computing capabilities (i.e., is not a "smart watch"), whereas in some embodiments, the wristwatch 200 does have embedded computing capabilities (i.e., is a smart watch).

The electronic device 100 is a wearable health and wellness device that attaches directly to the bottom of one's wristwatch 200. The computing device 300 may be one of many different types of computing devices including, but not limited to, a mobile phone, a standard personal computer, a smart phone, a notebook computer, a tablet computer, and user interface device, among others.

In some embodiments, the electronic device 100 is comprised of a small disc-shaped unit that attaches directly to the bottom of the wristwatch 200, or other wrist-worn device, via an attachment element. The electronic device 100 houses functional health and fitness tracking sensors and instrumentation that enables wearers of the electronic device 100 to monitor and track one or more physiological metrics. The electronic device 100 is able to attach to any wristwatch, wrist worn device, and/or wristwatch strap. In some alternative embodiments, the electronic device 100 can be embedded in a wristwatch, wrist worn device, and/or wristwatch strap.

In some embodiments, the electronic device 100 is able to transmit data to and receive data from the computing device 300 via a data connection 150. The data connection 150, in one example, is implemented via a short-range communication protocol, such as Bluetooth®. For example, in an embodiment where the computing device 300 comprises a mobile phone, the electronic device 100 is able to transmit data to and receive data from the mobile phone via a Bluetooth® connection between the electronic device 100 and the mobile phone. The data connection 150 may also be implemented in any other communication technology besides Bluetooth®.

The computing device 300 receives data captured by one or more sensors included in the electronic device 100 and processes or analyzes the data. In some embodiments, a result of processing or analyzing the data is transmitted back to the electronic device 100. An indication of the result can then be displayed on the electronic device, for example, via LEDs (light-emitting diodes) embedded in the electronic device 100.

In some embodiments, the electronic device 100 can be used as a motion control device. The housing of the electronic device 100 can include motion control sensors that can be used to control a variety of motion controlled devices. Some examples include video game controllers, gesture controllers for computer applications, and home automation.

In some embodiments, the computing device 300 is optionally connected to a server device 350 via a network connection 250. Examples of the network connection include a cellular network connection, wireless network connection, Bluetooth® connection, 3G and WiFi® radio connection in mobile computing devices, and USB (Universal Serial Bus), among others. In some embodiments, the data captured by one or more sensors included in the electronic device 100 that is received by the computing device 300 may be forwarded to the server device 350 for processing. In this manner, the computing device 300 performs less processing and may save battery power.

Figure 2:
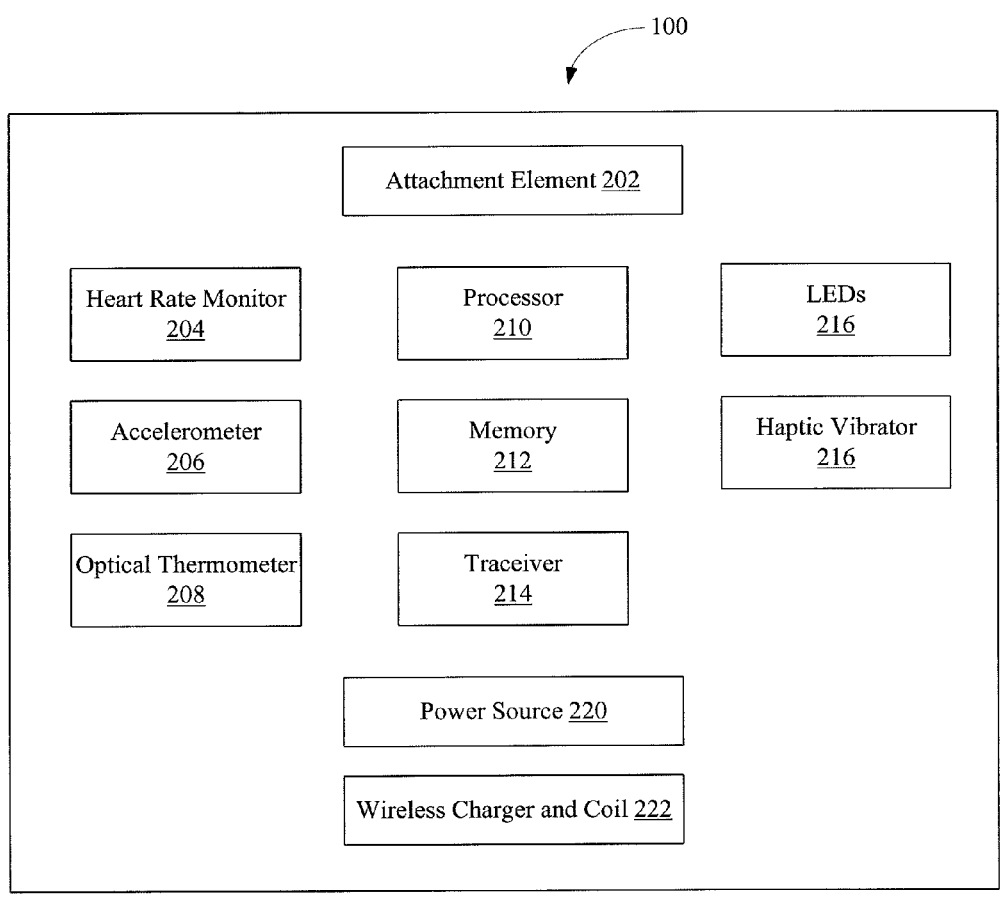
FIG. 2 is a block diagram of the electronic device of FIG. 1, according to one embodiment of the disclosure.

FIG. 2 is a block diagram of the electronic device 100 of FIG. 1, according to one embodiment of the disclosure. As shown, the electronic device 100 includes an attachment element 202, a heart rate monitor 204, an accelerometer 206, an optical thermometer 208, a processor 210, a memory 212, a transceiver 214, LEDs 216, a haptic vibrator 218, a power source 220, and a wireless charger and coil 222. The specific elements shown in FIG. 2 are not limiting, and other or different elements may be included in the electronic device in other embodiments.

In one embodiment, the electronic device 100 is encapsulated in a housing that is less than 40 mm in diameter and 4.5 mm in thickness. The housing is made of a polymer plastic case, but could also be made of a standard plastic, glass or metal, among others.

The attachment element 202 attaches the electronic device 100 to a wristwatch 200. In one embodiment, the attachment element 202 comprises micro suction tape. The micro suction tape may be one circular piece or multiple pieces in various shapes. The micro suction tape helps attach the housing firmly to the wristwatch 200, but also lets the electronic device 100 be taken off and put onto other wristwatches without leaving any residue. The micro suction tape does not lose its functionality with use and lets the electronic device 100 be taken on and off wristwatches easily.

In other embodiments, the attachment element may be one or more of adhesive, suction cups, suction cup tape, mechanical clasps to the edge or back of the wristwatch 200, mechanical clasps to the wristwatch straps, clasps to the lugs of the wristwatch case, clasps to wristwatch strap, pins or spring bars, and any other technically feasible mechanism for attaching a device to a wristwatch.

Also included within the electronic device 100 is a collection of physiological sensors, including an optical heart rate monitor 204, a motion accelerometer 206, and an optical thermometer 208. The rate monitor 204 and the optical thermometer 208 measure the heart rate and temperature, respectively, of the wearer of the wristwatch 200 with coupled electronic device 100. The motion accelerometer 206 is able to recognize specific activities of the wearer, such as sitting, driving a car, standing, walking, running, biking, swimming, certain other sports including tennis and golf, among others.

The electronic device 100 can also include other sensors (not shown) such as, but not limited to, electrocardiography ("EKG") heart rate sensors, global positioning system ("GPS") sensors, altimeters, body mass index ("BMI") sensors, and piezoelectric sensors. The measurements taken by the various sensors included in the electronic device 100, including the heart rate monitor 204, the motion accelerometer 206, and the optical thermometer 208, among others, is stored in a memory 212. Examples of such memory 212 may include non-volatile storage elements include magnetic hard disks, optical discs, floppy discs, flash memories, or forms of electrically programmable memories (EPROM) or electrically erasable and programmable (EEPROM) memories, as well as volatile memories such as random access memories (RAM), dynamic random access memories (DRAM), and static random access memories (SRAM). Memory 212 also stores program instructions for execution by one or more processors 210. The processor 210 is programmed and connected to deliver commands and receive information from the sensors within the electronic device 100 and the computing device 300.

The electronic device 100 also includes a transceiver 214 for transmitting and receiving data. The transceiver 214 may be wired or wireless. For example, the transceiver 214 may be a Bluetooth® transceiver. In general, transceiver 214 is a communication unit that can wirelessly communicate with computing device 300. Transceiver 214 can also communicate with other wireless communication enabled devices, such as wireless enabled electronics including light bulbs and garage door openers.

The electronic device 100 includes one or more LEDs 216. In one embodiment, the LEDs 216 are arranged in a ring around the edge of the housing of the electronic device 100. The electronic device 100 also includes a haptic vibrator 218. Via both the LEDs 216 and haptic vibrator 218, the wearer of electronic device 100 can receive information both visually, in the form of lights from the LEDs 216, and physically, in the form of vibrations from the haptic vibrator 218 to help measure performance, monitor status, and receive notifications. Electronic device 100 also includes a power source 220 that provides power to other elements of the electronic device. In one embodiment, the power source 220 is a rechargeable battery that is recharged via wireless charger and coil 222.

The electronic device 100 may include other elements that are not shown in FIG. 2, such as a camera, speakers, or a display screen.

Figure 3A:
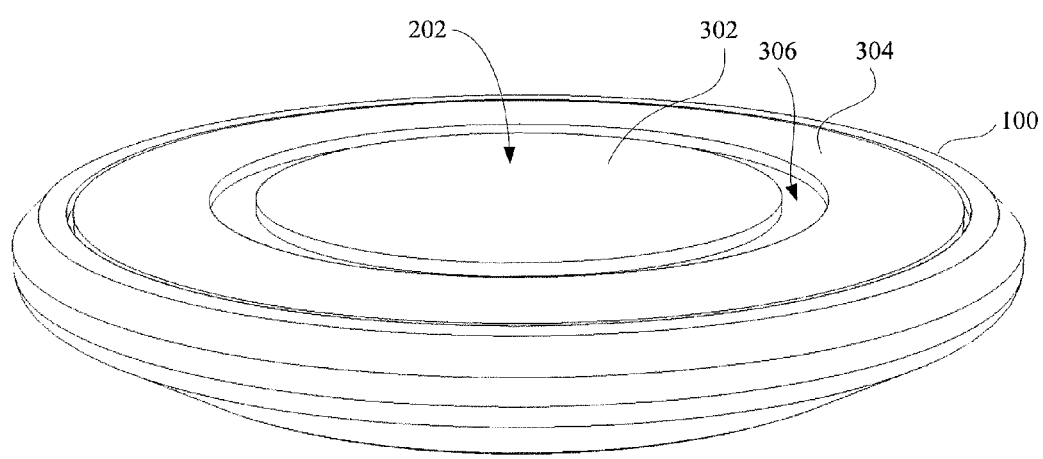
FIG. 3A is a perspective view of an electronic device capable of being coupled to a wristwatch, according to one embodiment of the disclosure.

FIG. 3A is a perspective view of an electronic device 100 capable of being coupled to a wristwatch 200, according to one embodiment of the disclosure. As shown, the electronic device 100 has a circular shape. In one example embodiment, the electronic device 100 is encapsulated in a housing that is less than 40 mm in diameter and 4.5 mm in thickness. In the example shown in FIG. 3A, the attachment element 202 comprises micro suction tape. The micro suction tape includes two portions 302 and 304. Portion 302 is a circular-shaped portion, and portion 304 is a ring-shaped portion 304. There is a small gap 306 between the portions 302 and 304.

With reference to FIG. 3A, the electronic device 100 housing may be comprised of several pieces of polymer plastic, standard plastic, glass or metal that are sealed together using waterproof sealant or are thermo-welded together to make the housing completely waterproof. In one embodiment, the electronic device 100 has two faces, a bottom face and a top face. The bottom face is flat and includes the micro suction tape. The electronic device 100 attaches to the wristwatch via the bottom face. In some embodiments, the top face, which rests against a user's skin, is domed or curved. At the peak of the dome is a clear lens through which the optical sensors such as the optical heart rate monitor 204 and the optical thermometer 208 take measurements from the wearer. The clear lens can be made of clear polymer plastic, plastic, or glass.

Figure 3B:
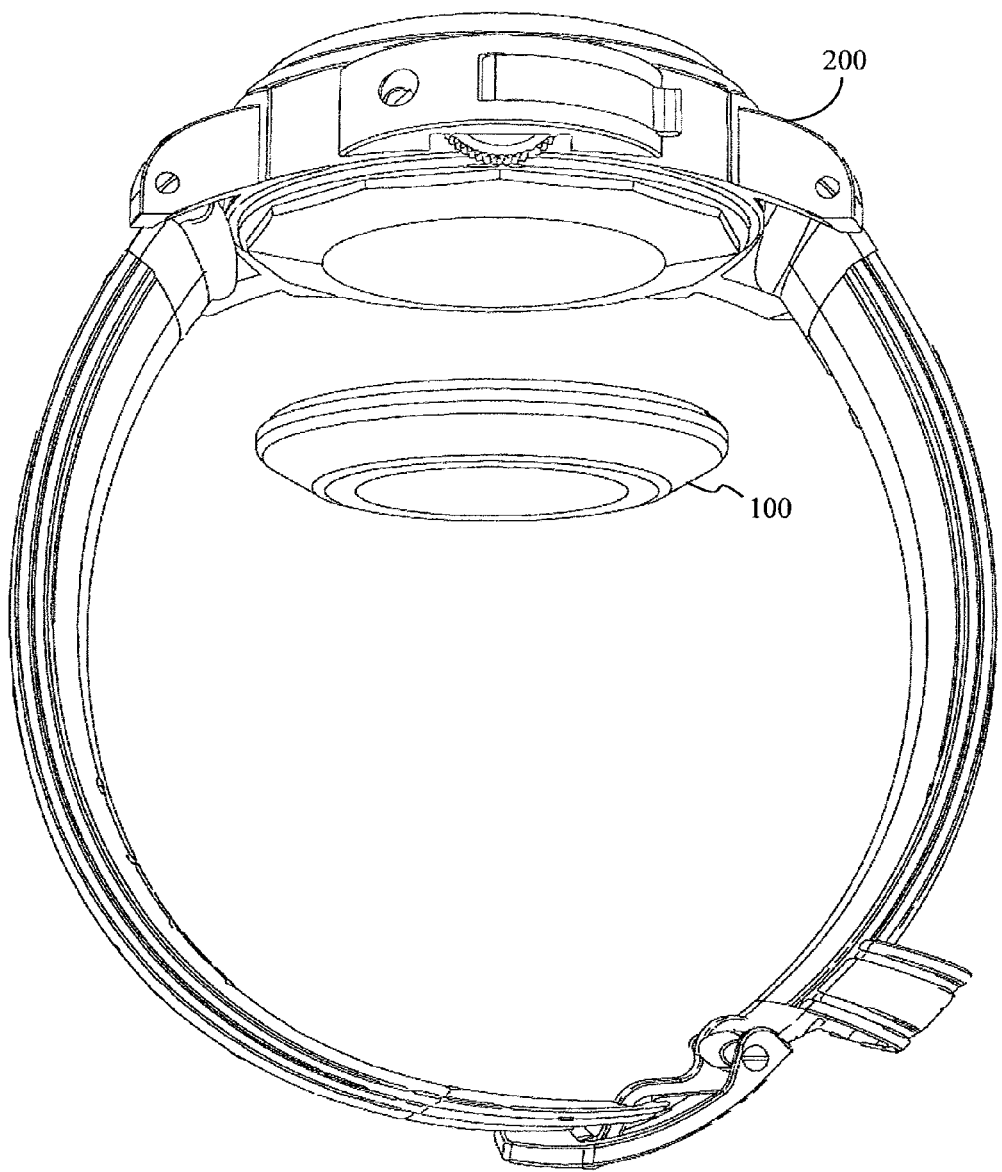
FIG. 3B is a perspective view of an electronic device and wristwatch, according to one embodiment of the disclosure.
Figure 3C:
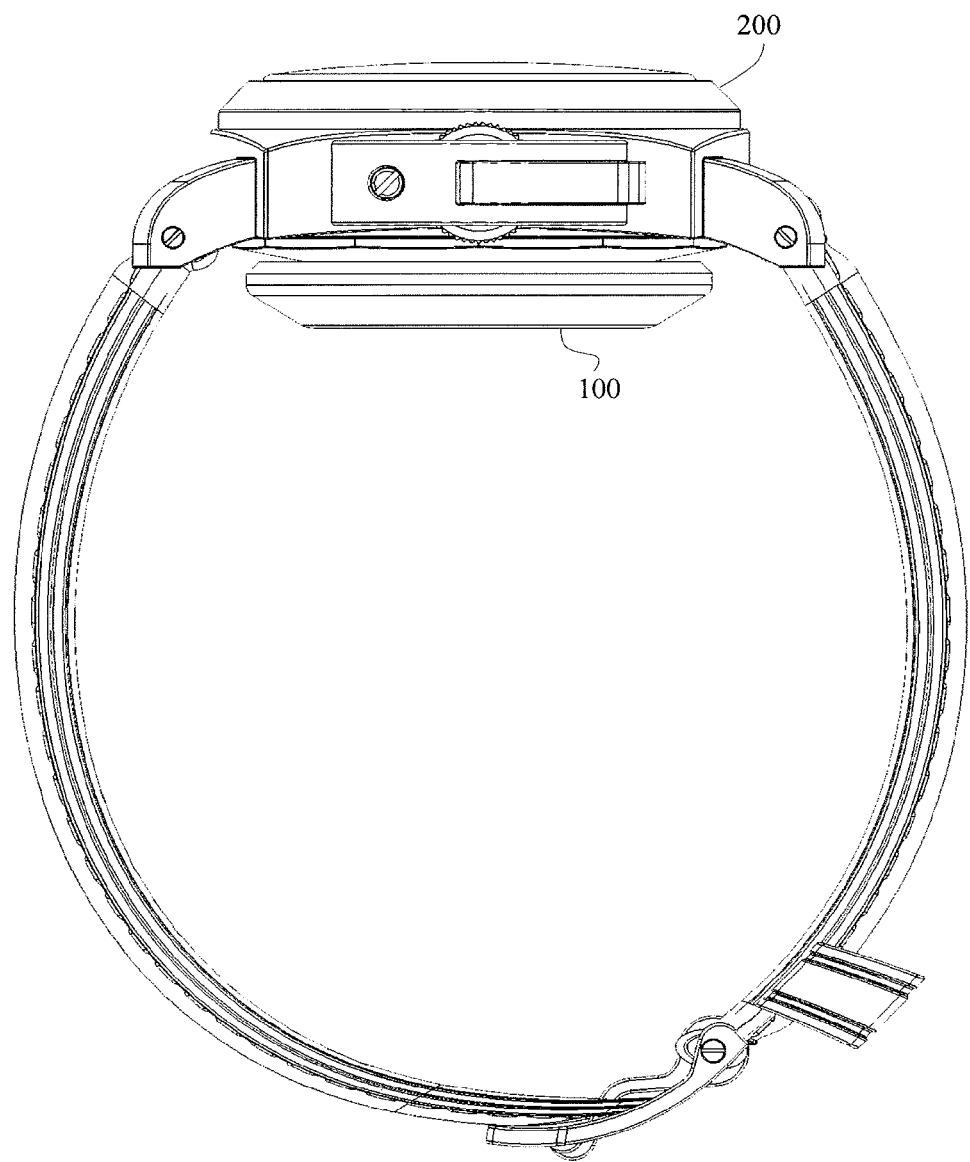
FIG. 3C is a side view of an electronic device and wristwatch, according to one embodiment of the disclosure.

FIG. 3B is a perspective view of an electronic device 100 and wristwatch 200, according to one embodiment of the disclosure. FIG. 3C is a side view of an electronic device and wristwatch, according to one embodiment of the disclosure. As shown, the electronic device is capable of being positioned on the bottom of the wristwatch face. As such, in some embodiments, the electronic device 100 acts as a "wristwatch pedestal" that lifts the wristwatch off of the wrist. In some implementations, this adds improved wristwatch readability, improves the aesthetic view of the wristwatch, and for people with small wrists, it adds extra space to fit both a watch that has too large a face for one's wrist as well as extra space to fit a wristwatch that's strap that is too big for one's wrist.

Figure 4:
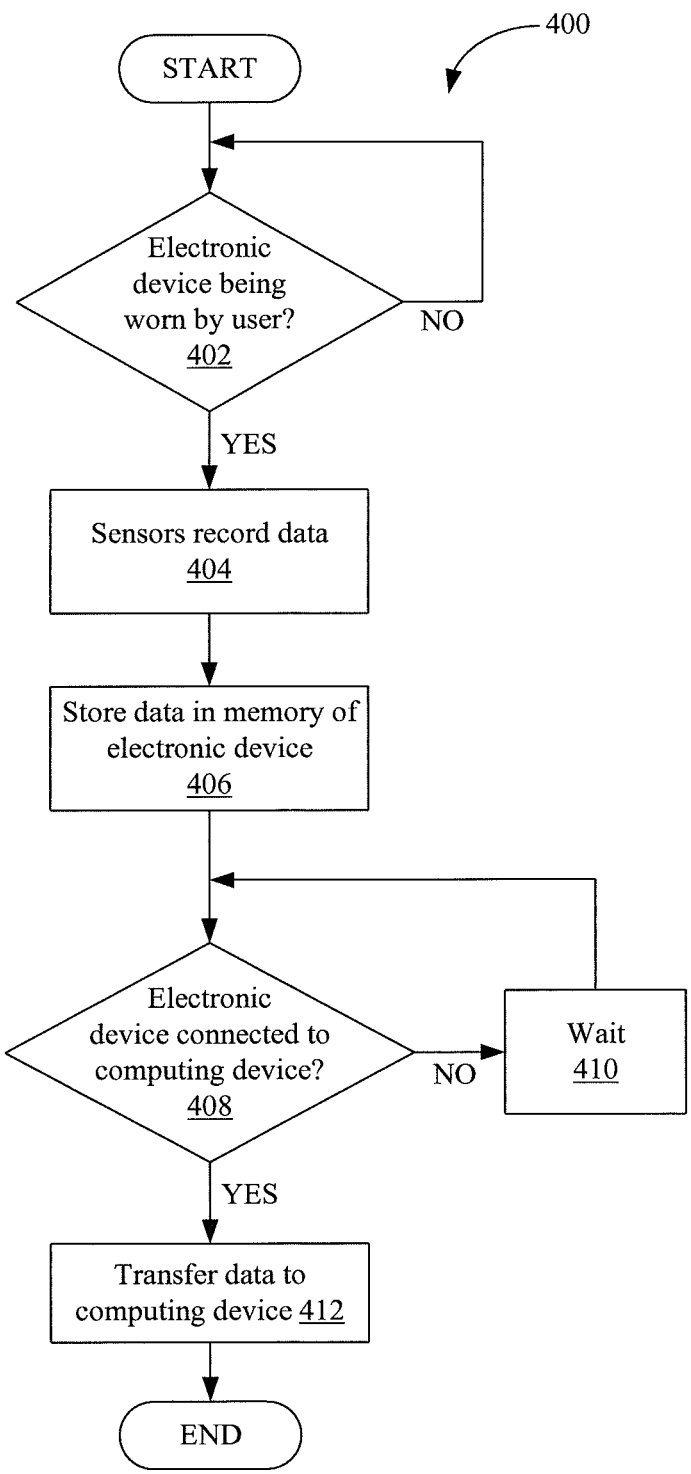
FIG. 4 is a flow diagram of method steps for operating an electronic device capable of being coupled to a wristwatch, according to one embodiment of the disclosure.

FIG. 4 is a flow diagram of method steps for operating an electronic device capable of being coupled to a wristwatch, according to one embodiment of the disclosure. The method 400 begins at step 402, where an electronic device determines whether the electronic device, such as electronic device 100 in FIG. 1, is being worn by the user. For example, the electronic device can detect that it is being worn by the user when the electronic device is turned on, the electronic device is connected to computing device 300 via Bluetooth or other wireless connection, and/or the electronic device recognizes that it is being worn due to the temperature sensor 208 having a reading indicative of being worn by the user. If it is not determined that the electronic device is being worn, then the method 400 continuously loops to step 402 until it is determined that the electronic device is being worn.

If, at step 402, the electronic device determines that the electronic device is being worn by the user, then the method 400 proceeds to step 404, where one or more sensors within the electronic device start recording data. At step 406, the data recorded by the one or more sensors is stored in a memory included in the electronic device.

At step 408, electronic device determines whether the electronic device is connected to a computing device, such as computing device 300 in FIG. 1. If the electronic device determines that the electronic device is not connected to a computing device, then the method 400 proceeds to step 410, where the electronic device waits for some predetermined amount of time. For example, the electronic device may wait for one minute.

If, at step 408, the electronic device determines that the electronic device is connected to a computing device, then the method 400 proceeds to step 412, where the electronic device transfers the recorded sensor data to the computing device. The data can be transferred via Bluetooth® or other wireless connection. An application or "app" can be installed on the computing device that allows the data that was transferred from the electronic device to be viewed via the application. The computing device may also transmit the received data to a server, enabling the data to be accessed via a website or other application.

As described, in one embodiment, the electronic device is able to transmit data to and receive data from a computing device via, for example, a short-range Bluetooth® communication protocol. The data transferred from the electronic device can be viewed via a website or mobile application live on a screen of the computing device. For example, in embodiments where the computing device is a mobile phone, a wearer can see their heart rate, body temperature, steps, stress levels and activity for the day, along with other metrics via a mobile application of the mobile phone.

Figure 5:
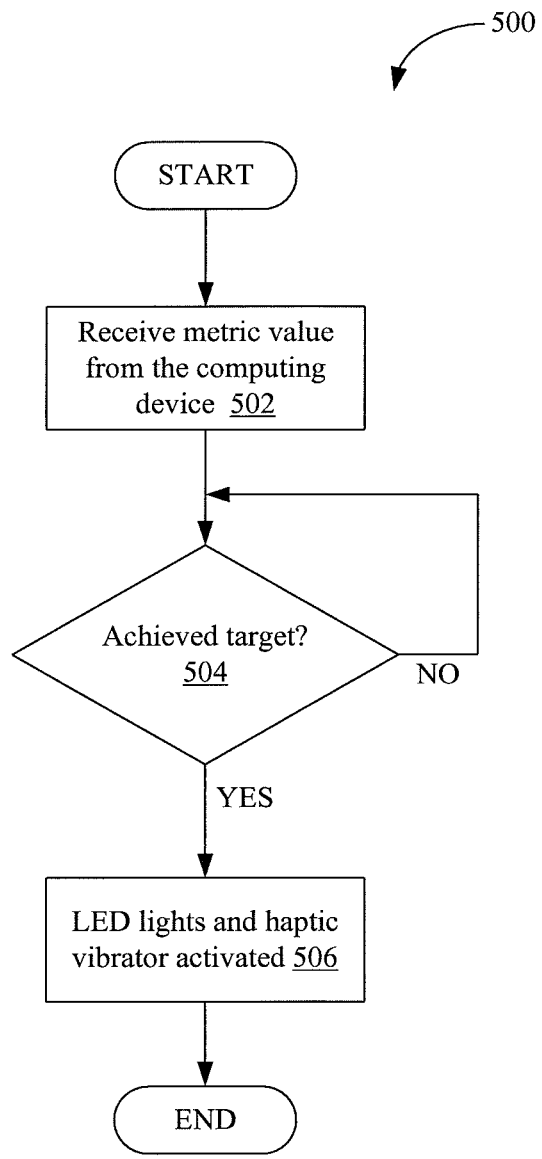
FIG. 5 is a flow diagram of method steps for displaying information on an electronic device capable of being coupled to a wristwatch, according to one embodiment of the disclosure.

FIG. 5 is a flow diagram of method steps for displaying information on an electronic device capable of being coupled to a wristwatch, according to one embodiment of the disclosure. According to various embodiments, a variety of information can be visualized and transmitted to the electronic device (e.g., electronic device 100) from the computing device (e.g., computing device 300). This information can be visualized and output via the LEDs 216 and/or the haptic vibrator 218 in the electronic device 100. The information includes, but is not limited to, flashing and vibrating notifications that the user has achieved a pre-targeted goal of walking a certain number of steps, flashing and vibrating notifications that the user is receiving an email, text message, or phone call and flashing and vibrating to show your live heart rate, among others.

In one example, as shown in FIG. 5, the electronic device notifies a user that the user has achieved a pre-targeted goal, e.g., a certain number of steps per day. As shown in FIG. 5, the method begins at step 500, where the electronic device receives a metric value from the computing device. The metric value may have been computed by the computing device (or by a server device) based on sensor data transmitted from the electronic device to the computer device (or server device).

At step 504, the electronic device determines whether the received metric value indicates that the user has achieved a target goal, e.g., a number of steps for the day. If the electronic device determines that the received metric value does not indicate that the user has achieved the target goal, then the method 500 returns to step 504.

If the electronic device determines that the received metric value indicates that the user has achieved the target goal, then the method 500 proceeds to step 506. At step 506, the electronic device causes the LED lights 216 and/or the haptic vibrator 218 included in the electronic device to be activated to flash and/or vibrate, respectively, in a particular pattern and colors that corresponds to the user achieving their goal.

As described, there many different sensors can be included in the electronic device that are able to record different metrics including heart rate, stress, body temperature and activity, among others. To make accessing the data easier, calculations can be performed on the data captured by the sensors in the electronic device to combine the data into a single wellness score. For example, the calculations can be performed by the electronic device itself, by a computing device that is in communication with the electronic device, or by a server communicatively coupled to the computing device. A result of the calculations can be displayed in an application executing on the connected computing device, or may be displayed by the electronic device. In some embodiments, this single wellness score is an easy way for a user to get a quick glanceable update on the user's status or progress.

Figure 6:
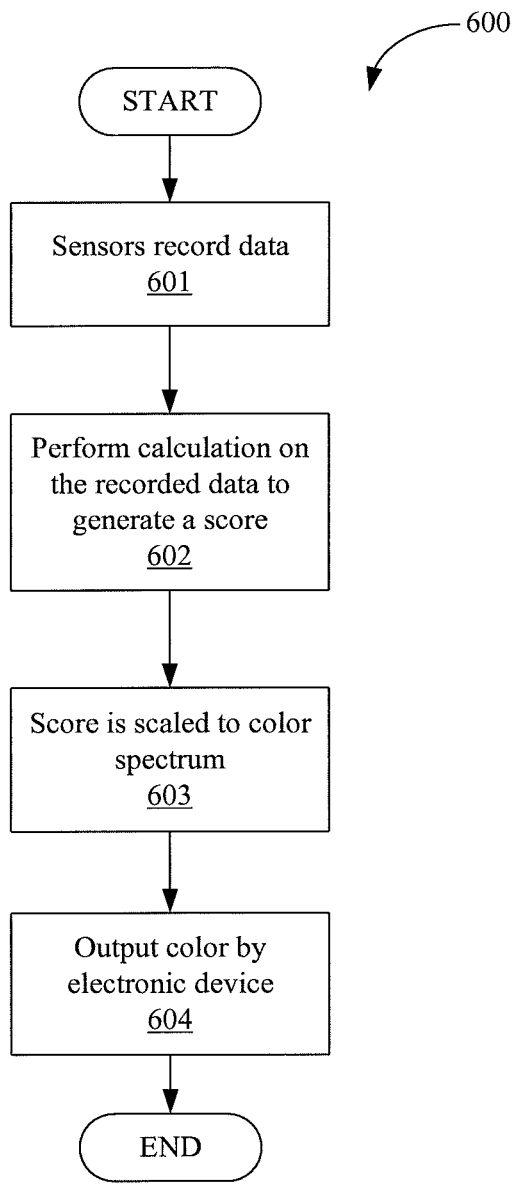
FIG. 6 is a flow diagram of method steps for calculating and displaying an indication of a wellness score on an electronic device capable of being coupled to a wristwatch, according to one embodiment of the disclosure.

FIG. 6 is a flow diagram of method steps for calculating and displaying an indication of a wellness score on an electronic device capable of being coupled to a wristwatch, according to one embodiment of the disclosure. As shown, the method 600 begins at step 601, where one or more sensors included in an electronic device collect and record sensor data. In some embodiments, the recorded data is also transmitted to a computing device communicatively coupled to the electronic device.

At step 602, calculations are performed on the recorded sensor data to generate a score. In one embodiment, the calculations comprise calculating a weighted average of the recorded sensor data. According to various embodiments, the calculations performed at step 602 can be performed by a processor included in the electronic device or by a processor included in the computing device communicatively coupled to the electronic device. In some embodiments, the calculated score is also transmitted to a computing device communicatively coupled to the electronic device.

At step 603, the calculated score is scaled to a color spectrum and a color corresponding to the score is calculated or selected. In one embodiment, the calculated score can be quartiled. For example, the first, second, third and fourth quartiles can then be scaled to a color spectrum, which would correspond to red, yellow, green and blue, respectively. For example, if the calculated score is in the second quartile, then the corresponding color output by the LEDs 216 is yellow.

At step 604, the electronic device outputs one or more colors corresponding to the calculated score. The colors can be output via LED lights embedded in the electronic device. In one example, the LED lights may display a green color if a certain goal is achieved, the LED lights may display a red color if a certain goal was not achieved, or may display a yellow color if a certain goal has not yet been achieved but is expected to be achieved if the user maintains current activity levels.

In some embodiments, the electronic device 100 includes a motion accelerometer 206 that tracks movement of the electronic device 100. In some embodiments, the accelerometer 206 can recognize a tapping motion. Because the electronic device 100 is firmly attached to a user's wristwatch 200, the user can tap anywhere on the electronic device 100, on the wristwatch 200, or even on the user's wrist, to engage a tap recognition workflow within the electronic device 100, as described below.

Figure 7:
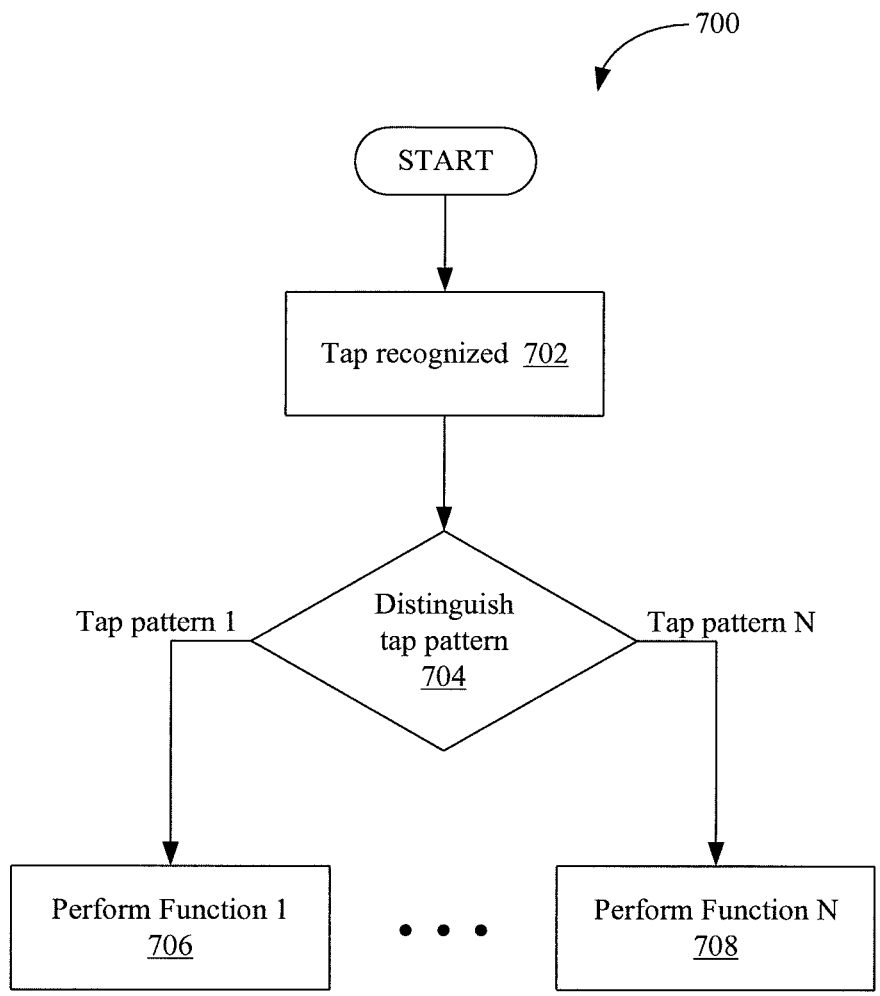
FIG. 7 is a flow diagram of method steps for receiving a tapping pattern on an electronic device capable of being coupled to a wristwatch, according to one embodiment of the disclosure.

FIG. 7 is a flow diagram of method steps for receiving a tapping pattern on an electronic device capable of being coupled to a wristwatch, according to one embodiment of the disclosure. As shown, the method 700 begins at step 702, where the electronic device detects that a tap pattern has been received. For example, the processor included in the electronic device can recognize a tap based on certain characteristics of the accelerometer data.

Once the electronic device detects that a tap pattern has been received, the method 700 proceeds to step 704, where the electronic device distinguishes the tap pattern from one of a plurality of tap patterns. In some embodiments, a user can program what function that the user wants the electronic device to perform when a tap is received. For instance, a user could program the electronic device to show a current wellness score for the last hour by tapping once, could program the electronic device to show a heart rate by tapping twice, and could program the electronic device to show the user how many hours of battery life are left by tapping three times.

For example, in FIG. 7, if at step 704 tap pattern 1 is detected, the method 700 proceeds to step 706, where function 1 corresponding to tap pattern 1 is performed. If at step 704 tap pattern N is detected, the method 700 proceeds to step 708, where function N corresponding to tap pattern N is performed. Any number of tap patterns and corresponding programmed functions can be enabled on the electronic device.

In some embodiments, along with communicating data to a computing device 300, the electronic device 100 can also turn on features within the computing device 300. One example includes turning on a GPS tracker when recognizing that the user is going for a run, and turning off the GPS tracker when the user is finished with the run. Another example includes turning on specific applications of the computing device 300 that track certain activities when the electronic device 100 recognizes that those activities have started. Yet another example is turning on a music application and causing the computing device 300 to play music. This ability to seamlessly turn on or enable other features of the computing device 300 can also extend to other devices in the user's home, such as turning on lights when the user enters a room or opening a garage door when the user pulls in to a driveway at home.

Figure 8:
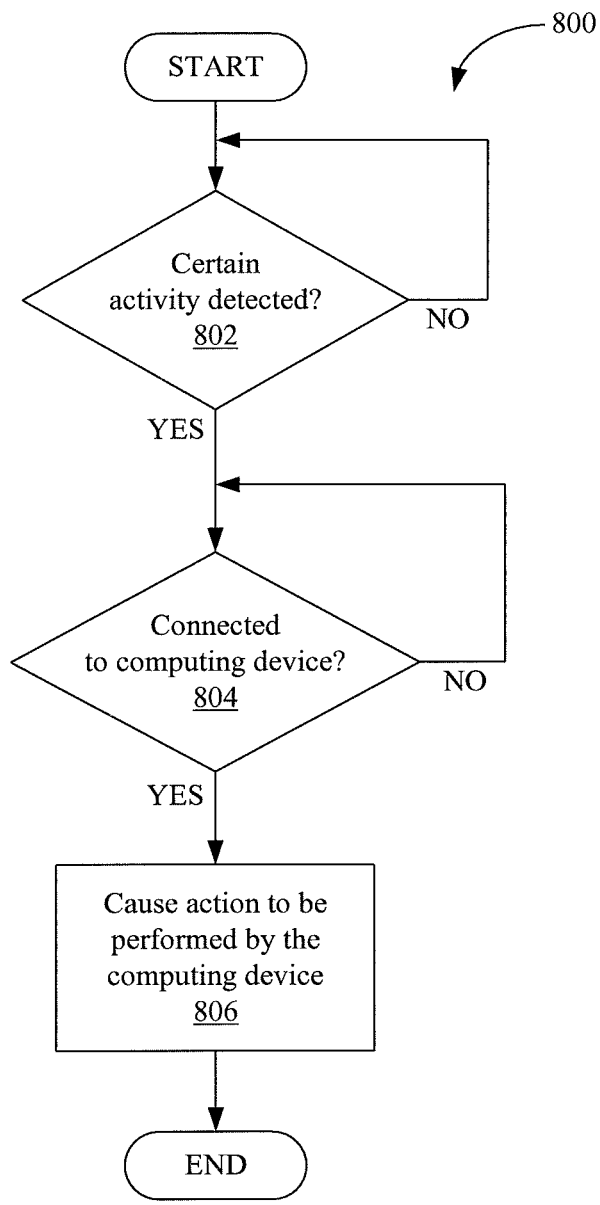
FIG. 8 is a flow diagram of method steps for executing an application on a computing device communicatively coupled an electronic device capable of being coupled to a wristwatch, according to one embodiment of the disclosure.

FIG. 8 is a flow diagram of method steps for executing an application on a computing device communicatively coupled an electronic device capable of being coupled to a wristwatch, according to one embodiment of the disclosure. The method 800 begins at step 802, where the electronic device determines whether a certain, predetermined activity has been detected. Examples of such activities include going on a run, entering a room, pulling into a driveway, etc.

If, at step 802, the electronic device does not detect a predetermined activity, then the method 800 continuously loops to step 802 until the electronic device detects a predetermined activity. If, step 802, the electronic device detect a predetermined activity, then at step 804 the electronic device determines whether the electronic device is connected to a computing device. If the electronic device determines that the electronic device is not connected to a computing device, then method 800 continuously loops to step 804 until it is determined that the electronic device is connected to a computing device. If, at step 804, the electronic device determines that the electronic device is connected to a computing device, then the method 800 proceeds to step 806, where the electronic device causes an action to be performed by the computing device. For example, the electronic device may send a signal to the computing device to effectuate a certain event. Non-limiting examples of such an event to be performed by the computing device include turning on the GPS tracker or executing a certain application of the computing device.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Variations of the embodiments disclosed herein may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An electronic device, comprising:
    a housing;
    an attachment portion capable of coupling the housing to a bottom of a wristwatch to be worn by a wearer;
    one or more physiological sensors included in the housing that measure one or more physical phenomena corresponding to the wearer of the wristwatch and electronic device coupled to the wristwatch;
    a memory configured to store data corresponding to the one or more physical phenomena; and
    a wireless communication device included in the housing for communicating the data to a computing device in wireless communication with the electronic device.

2. The electronic device of claim 1, wherein the one or more physiological sensors include one or more of a heart rate sensor, a motion accelerometer, and a thermometer.

3. The electronic device of claim 1, wherein the computing device comprises a mobile phone.

4. The electronic device of claim 1, wherein the attachment portion comprises suction tape that adheres to the bottom of the wristwatch.

5. The electronic device of claim 1, wherein the attachment portion comprises one or more of adhesive, suction cups, suction cup tape, mechanical clasps to the edge or back of the wristwatch, mechanical clasps to a strap of the wristwatch, mechanical clasps to lugs of the wristwatch, pins, and spring bars.

6. The electronic device of claim 1, wherein the wireless communication device is capable of implementing Bluetooth® protocol.

7. The electronic device of claim 1, further comprising:
    a processor configured to calculate a wellness score for the wearer of the wristwatch and electronic device coupled to the wristwatch based on the data corresponding to the one or more physical phenomena; and
    one or more output devices included in the electronic device to output an indication corresponding to the wellness score.

8. The electronic device of claim 7, wherein calculating the wellness score comprises computing a weighted average of the data corresponding to the one or more physical phenomena.

9. The electronic device of claim 7, wherein the one or more output devices comprise one or more light-emitting diodes (LEDs) configured to illuminate in different colors corresponding to the wellness score.

10. The electronic device of claim 7, wherein the one or more output devices comprise a haptic vibrator configured to vibrate in a manner corresponding to the wellness score.

11. The electronic device of claim 1, wherein the housing comprises:
    a first face that couples the attachment portion to the bottom of the wristwatch, wherein the first face is flat; and
    a second face opposite the first face that is capable of resting against skin of the wearer of the wristwatch and electronic device coupled to the wristwatch, wherein the second face includes a clear lens through which the one or more physiological sensors are capable of measuring the one or more physical phenomena corresponding to the wearer.

12. A method for operating an electronic device, the method comprising:
    detecting that the electronic device is being worn a wearer, wherein the electronic device is coupled to a bottom of a wristwatch worn by the wearer;
    measuring, using one or more physiological sensors included in the electronic device, one or more physical phenomena;
    storing data corresponding to the one or more physical phenomena in a memory included in the electronic device; and
    transmitting the data corresponding to the one or more physical phenomena to a computing device in wireless communication with the electronic device.

13. The method of claim 12, wherein the one or more physiological sensors include one or more of a heart rate sensor, a motion accelerometer, and a thermometer.

14. The method of claim 12, wherein the electronic device is coupled to the bottom of the wristwatch worn by the user via suction tape that adheres to the bottom of the wristwatch.

15. The method of claim 12, further comprising:
    calculating a wellness score based on the data corresponding to the one or more physical phenomena; and
    outputting, via one or more output devices included in the electronic device, an indication corresponding to the wellness score.

16. The method of claim 15, wherein calculating the wellness score comprises computing a weighted average of the data corresponding to the one or more physical phenomena.

17. The method of claim 15, wherein the one or more output devices comprise one or more light-emitting diodes (LEDs) configured to illuminate in different colors corresponding to the wellness score.

18. The method of claim 15, wherein the one or more output devices comprise a haptic vibrator configured to vibrate in a manner corresponding to the wellness score.

19. The method of claim 12, wherein detecting that the electronic device is being worn comprises determining that a temperature value of a temperature sensor included in the electronic device is indicative of the electronic device being worn.

20. A computer-readable storage medium storing instructions that, when executed by a processor, cause a computer system to operate an electronic device, by performing the steps of:
    detecting that the electronic device is being worn a wearer, wherein the electronic device is coupled to a bottom of a wristwatch worn by the wearer;
    measuring, using one or more physiological sensors included in the electronic device, one or more physical phenomena;
    storing data corresponding to the one or more physical phenomena in a memory included in the electronic device; and
    transmitting the data corresponding to the one or more physical phenomena to a computing device in wireless communication with the electronic device.

21. The computer-readable storage medium of claim 20, further comprising:
    calculating a wellness score based on the data corresponding to the one or more physical phenomena; and
    outputting, via one or more output devices included in the electronic device, an indication corresponding to the wellness score.

\* \* \* \* \*